United States Patent [19]
Riera

[11] Patent Number: 5,116,225
[45] Date of Patent: May 26, 1992

[54] ANGULATED ABUTMENT FOR OSSEOINTEGRATED IMPLANTS

[76] Inventor: Juan C. A. Riera, Brasil 838, Salto, Uruguay

[21] Appl. No.: 668,969

[22] Filed: Mar. 13, 1991

[30] Foreign Application Priority Data

Oct. 17, 1990 [UY] Uruguay ................................ 23.140

[51] Int. Cl.⁵ .............................................. A61C 8/00
[52] U.S. Cl. ..................................... 433/173; 433/174
[58] Field of Search ................................ 433/173, 174

[56] References Cited

U.S. PATENT DOCUMENTS 4,531,915  7/1985  Tatum, Jr. ........................... 433/173
4,854,872  8/1989  Detsch ................................ 433/174

FOREIGN PATENT DOCUMENTS

0323421  5/1989  European Pat. Off. ............ 433/173

Primary Examiner—John J. Wilson
Attorney, Agent, or Firm—Body, Vickers & Daniels

[57] ABSTRACT

An angulated abutment system for affixing a dental prosthesis to an anchor implanted in the jaw bone such that the dental prosthesis can be mounted axially offset from the axis of the implant. Two components of the abutment system are designed in such a manner to allow the dental prosthesis to be adjusted in small angles of rotation.

22 Claims, 7 Drawing Sheets

ANGULATED ABUTMENT FOR OSSEOINTEGRATED IMPLANTS

BACKGROUND OF THE INVENTION

This invention relates to dental prosthesis mounted over metal implants anchored to the bone.

The procedure is based upon a titianium part analog to a tooth root which by means of a known and elaborated surgical technique is fixed to the patient's bone. This implant serves as the base upon which a transmucosal intermediate member is attached serving this latter as support for the final prosthesis to be fixed upon.

Given the need to replace natural missing teeth, there has been a large amount of research in the dentistry field leading to the findings of Brånemark in the 1960's. The present practice starts with a surgical procedure that carefully and with the minimal trauma, places a titanium plug in the patient's bone. This implant is left in place covered by the sutured gum, undisturbed and without any loads being applied to it, for 4 to 6 months prior to the final stage. After that time, a prosthesis is fixed to the anchored implant usually by means of intermediate members.

At the present time there are several types of implant-supported prosthesis systems in use (Core-Vent, Nobelpharma, Calcitek, IMZ, etc.). These systems comprise small plugs, generally cylindrical, sometimes self tapping screws, of 3 to 6 milimeters in diameters and 6 to 22 milimeters in length, that are anchored in the bone. Onto these plugs the prosthesis are fixed by means of different members varying in number, form and function according to the chosen system. A transmucosal spacer member, usually known as an abutment, is generally used to connect the final prosthesis to the implanted anchor. In some cases a gold cylinder is used as the connecting link between the abutment and the final crown, being fixed to the titanium plug by means of a screw and becoming, after casting, an integral part of the prosthesis. In other systems a plastic sheath is used instead of the cylinder; it melts away with the waxing material in the moulding process leaving a cavity for the fixing screw.

The anatomy of each individual patient places limitations on the direction of the implant. The reposition of missing teeth is generally done over patients that have suffered some degree of bone loss. In addition maxillary sinus grows in those places where there are no teeth. The width of the available jaw bones is another determinant factor for the placement of the anchor. The combination of these and other individual features of the patient makes it usually impossible for the direction of the main axis of the implanted plug to be that required for the final prosthesis' alignment.

The first implants made were done only on those patients in which the characteristics of the jaw bone was such that allowed the axis of the implanted anchor be the same as the required by the prosthesis. This fact limited the implants to the anterior part of the lower jaws between the mandibular foramina; and in the upper jaws between maxillary sinuses or where adecuate space was available. These characteristics accounted for the fact that the majority of the early patients were complete endentulous.

Later on, different companies offered abutments that partially compensated for this non alignment of the implanted plug with the prosthesis. They enable the placement of the implanted anchor in places where the direction of its main axis would not be optimal for the final prosthesis. This was accomplished by means of angulated transmucosal spacer members or abutments having the axis of the emergent part in a direction different from that of the implant's axis. Some required intermediate laboratory casting procedures involving many time consuming sesions. Another type of intermediate abutment was to be bent to accommodate the final position. These bendable abutments were criticized because remnant stresses weakened the part. Recently new types of angulated abutment are available in the market. They are preangulated and can be rotated to different positions to achieve the desired direction; afterwards they are fixated.

Of this latter type, Nobelpharma offers an "Angulated abutment, complete, titanium, catalog number SDCA 102." "The angulated abutment has a twelve-sided internal design that locks onto the hexagon on the top of the fixture. This design allows the abutment to be rotated and locked down in twelve different positions on top of the fixture (implanted anchor). This will provide alternatives in order to achieve ideal abutment alignment to compensate for fixtures angled in different directions." This angulated abutment has the shortcoming that is "not intended for single tooth treatment due to the fact that there is no absolute interlock between the gold cylinder and the abutment to prevent rotation". Quoted from "Angulated Abutment, Clinical Procedure and Case Presentation", Nobelpharma 1989.

Similarly, Implant Innovations, Inc. offers a "pre-angled abutment and screw" (Pat. Pending) catalog numbers PA152, PA154, PA156, PA252, PA254, PA256, PA352, PA354, PA356. The following is quoted from Implant Innovations' catalog: "Pure titanium abutment for correction of non-parallel Brånemark type implants. Available in 15, 25 and 35 degree angle corrections and 2, 4, an 6 mm trans-tissue heights. Can be rotated to 12 different positions on the implant. Non rotational geometry allows for single tooth replacement. Cemented (15 degree) or screw retained (25 and 35 degree). Wax to abutment and cast telescopic crown to fit the abutment." The casting procedure is not so accurate as it is with those systems that use an intermediate gold cylinder telescopically mounted on the abutment. As it is the case with the Nobelpharma's angulated abutment this systems allows only 12 different azimuth positions around the main axis of the implanted anchor.

Core-Vent Corporation offers two kinds of angulated abutments, each of them coming in a series to cover different specific cases. One of these is manually bendable using appropriate tools. This type does not give an precise angulation and is also weakened by remnant stresses. The other kind requires the casting of a custom made abutment, and includes a stainless steel housing for the fixation of the prosthesis by means of a titanium screw. Associated with this type are a larger number of visits to the clinic and a time consuming laboratory procedure which affects the final cost. None of these types is as accurate as those that use pre-angulated parts attached to one another by means of screws.

Besides these mentioned examples, there are others that give partial answer to some of the problems stated earlier.

SUMMARY OF THE INVENTION

The subject of this invention is a set of interrelated parts that substitute the angulated abutments presently used to fix a final prosthesis to a titanium implant anchored in the jaw bones. It overcomes the problems presented by the devices now in use for direction corrections and offers a wider range of possibilities for the prosthetic procedures. The final purpose of the invention is to allow the dentist to give the emergent abutment the optimal direction needed by the prosthesis, independently of the direction of the main axis of the anchored implant.

In order for the description to be better understood we define the longitudinal axis of the anchored titanium implant as its main axis. All other directions are going to be related to this axis, being it the inclination of the final prosthesis' axis or the rotation of the abutment in a plane normal to the axis: azimuth.

At the present time, the direction of the abutment axis to that of the implanted anchor is limited. At the most a change in rotation of ±30° in a plane normal to the implant's axis is possible in some cases due to a 12 sided hollow in the base of the pre-angulated abutment that fits on the implant. The abutment design presented here allows for 30 positions at 12° azimuth angles on an implant with a six-sided recessed end, and 60 different positions with 6° in between on those having a protruding hexagon. Besides this flexibility, and given the rotational interlock between its component parts, the new abutment can be used in single-tooth treatments.

To the existing titanium implant a series of six different parts are sequentially attached ending with a gold cylinder or a plastic sheath that serves as the basis upon which the crown is to be built. We are taking an implant with a six sided end on its upper surface as the basis for this description and the differences for the other type of anchor are noted.

The first part in contact with the implant is a tapered flat cylinder of approximately 1.33 mm in height having the diameter of its smaller, lower, end that of the implant's cylindrical top section. This part can be fabricated with different heights to match that of the gum. It is also made of titanium and has a twelve sided hollow on its lower surface for it to be mounted on the implant. The version to fit on a recessed end implant has an hexagon matching the plug's end. The rotation of this part on top of the anchor during the procedures at the clinic allows for 12 different positions at 30 degree angles in one case and six positions at 60 degree angles in the other. The larger base, farther from the implant, is approximately 4 mm in diameter and has on its center a protruding five sided end. A 1.5 mm hole runs through this part to allow for the passage of a fixing screw.

Over that part, a similar one made of the same material is fitted being the same for the two types of implant. It is also a truncated cone approximately 1.33 mm in height being its diameters approximately 4 mm for the smaller and 4.4 mm for its larger one. This part can be also fabricated with different heights to match that of the gum. Cut on its lower surface there is a 10 sided hollow that fits on the previous part's 5 sided end. The rotation of this latter part over the previous one will add or substract angles multiple of 36 degrees to the azimuthal rotation of the former part regarding the implant. Thus combining these two parts over the implant during the clinical procedure will give as a result the possibility of rotating the final prosthesis' support in intervals of as little as 6 degrees for the implant with a six sided end, and 12 degrees for that ending with a six sided hollow. This part has a centered 2 mm hole at the top changing to a 1.5 mm passing hole at a depth of about 1 mm, forming a shoulder for the fixing screw to bear on. Centered on the upper surface there is a 3.1 mm threaded end, of about 1 mm in height, serving for the attachment of the part going on top of it. At the factory, that said part is going to be cemented to this one, to definitely prevent the separation of the two. At the time of its placement on the implanted anchor this part together with the one cemented to it and the titanium screw that passes through it are treated as a simple and complete assembly.

To lock these two parts and the anchored implant together, a passing titanium screw is used, its total length being 7 mm and its thread diameter that of the implant in which is going to fit. A 2 mm diameter by 1 mm high head houses a hex hole for an Allen type wrench. During fabrication this screw is put in place between the previously described part and the one that follows.

On the threaded portion on the upper end of the part described secondly another titanium part is fixed. It is a truncated assymetrical cone with its upper surface cut at a given angle from a plane normal to its main axis. A whole set of these parts can be fabricated with angles of 5°, 10°, 15°, 20°, 25°, 30°, 35°, 40°, and 45° giving the dentist the option of placing the axis of the prosthesis at the desired angle from that of the anchored implant. The total height of the finished part is about 3.3 mm, its major diameter is smaller than that of the upper surface of the part it is attached to, leaving a shoulder for the mentioned gold cylinder or plastic sheath to bear upon. The smaller diameter at the top is about 3.1 mm. In the lower surface a 3.1 mm threaded hole allows for the engagement of the two pieces. On the top, a 1.8 mm diameter by approximately 1 mm depth threaded hollow will receive the final screw that will fix the prosthesis to the assembly. On the sides of this cylinder, four tappered faces are cut at 90 degree angles of each other giving the part a pyramidal shape. The function of these planes is that of securing a perfect interlock with the gold cylinder or the material replacing the plastic sheath that attaches onto this part thus preventing it from rotating. A 1.6 mm hole runs through the center of this part for an allen wrench to be used to tighten the fixing titanium screw once the final position is achieved. During fabrication the three above mentioned parts are assembled together: the two large pieces are screwed and cemented to one another having already the titanium screw inside. At the time of its placement on the implanted anchor this part together with the one cemented to it, and the titanium screw that passes through it, are treated as a simple and complete assembly. The cavity in which the screw is housed is large enough to allow the easy rotation of the 5 sided end-10 sided hollow interface while holding the assembly and the implant together.

A gold cylinder telescopically covers the part recently described. It is going to be attached to that part by means of a fixing gold screw and its function is to serve as the metal base for the final prosthesis to be built upon. It is a slightly tappered 3.25 mm diameter, 4.2 mm high cylinder with a 0.4 mm high, 0.1 mm deep grove running around it at about 2.5 mm from the top. Inside this gold cylinder provisions are taken to allow for the following: 1. at the bottom, a cavity is left matching the tappered cylinder previously described but with enough clearance as to allow for only the rim of its base to rest on the shoulder left on the part described in second term. This implies that the lower edge of the gold cylinder is cut through a plane that it is not normal to its axis but forms an angle to it as it is the case with the truncated cone described earlier. A whole set of gold cylinders is required with lower edges cut at different planes to match the mentioned set of cones. 2. at the top, a cavity is left to house a gold screw passing through the part and threading into the truncated cone.

A plastic sheath replaces the gold cylinder if a recessed end titanium plug system is chosen. It melts away with the waxing material in the moulding process. It also has a cavity for the fixing screw and for the pyramid on which it will be set. Only the rim of its base will rest on the shoulder left on the part described secondly. This implies that the lower edge of the sheaths is cut through a plane that forms an angle with its axis as it is the case with the truncated cone described earlier. A whole set of plastic sheaths is required with lower edges cut at different planes to match the mentioned set of cones.

Finally, for a hexagon end type implant system, a gold screw is used to hold in place the prosthesis built on the gold cylinder. This is a 1.75 mm long, 1.8 mm diameter by 1 mm thread length, flat head, slotted screw. If the other type of system is used an 8 mm long, sloted screw with a cylindrical 3 mm diameter body holds the prosthesis to the rest of the abutment.

A slotted, 3 mm dia., 8 mm long guide pin is used to replace the said gold screw during the procedure for setting the abutment in the desired direction. Its lower end has a replica of the gold screw it replaces.

DESCRIPTION OF THE DRAWINGS

The parts just described are shown in the accompanying set of drawings.

The first part in contact with the implant is a tapered flat cylinder 2 having the diameter of its smaller end 21 that of the implant's cylindrical top section 11. It is made of titanium and has a twelve sided hollow 22 on its lower surface to fit on the implant's hexagon end 12. The version to fit on a six sided recessed end type implant has an hexagon 22 matching the plug's end 12. The larger diameter 23 has on its center a protruding five sided end 24. A 1.5 mm hole 25 runs through this part to allow for the passage of a fixing screw 4.

Over part 2, a similar one 3 made of the same material is fitted; the same part is used for the two types of implant. It is also a truncated cone and it too can be fabricated with different heights to help match that of the gum. Cut on its lower surface 31 there is a 10 sided hollow 33 that fits on the previous part's five sided end 24. As it has been said before, the rotation of part 3 over part 2 will add or substract angles multiple of 36 degrees to the azimuth rotation of the part 2 regarding the implant 1. Thus combining parts 2 and 3 over the implant 1 during the clinical procedure, will give as a result the possibility of rotating the final prosthesis' support in intervals of 6 degrees for the implant with a six sided end, and 12 degrees for that ending with a six sided hollow. Part 3 has a centered 2 mm dia. hole 34 at the top changing to a 1.5 mm passing hole 35, forming a shoulder 36 for the fixing screw 4 to bear on. Centered on the upper surface there is threaded end 37 serving for the attachment of part 5. At the factory, part 5 is going to be cemented to part 3, to definitely prevent the separation of the two; this is done having a titanium screw 4 already in its place between these parts. At the time of its placement on the implanted anchor, these two parts 3 and 5 together with titanium screw 4 are treated as a simple and complete assembly.

To lock parts 2 and 3 with the anchored implant 1, a passing titanium screw 4 is used. On its head 41, it houses a hex hole 43 for an Allen type wrench. Thread 42 is the same as the implant's 13. At the time of fabrication, screw 4 is put in place between the previously described part 3 and the one that follows 5.

On the threaded portion on the upper end 37 of part 3, another titanium part 5 is fixed. It is a truncated asymetrical cone with its upper surface 51 cut at a given angle 52 from a plane 59 normal to its main axis. A whole set of these parts can be fabricated with angles 52 at 5°, 10°, 15°, 20°, 25°, 30°, 35°, 40°, and 45° giving the dentist the option of placing the axis of the prosthesis 9 at the desired angle from that of the anchored implant. Part's 5 major diameter is smaller than that 32 of the upper surface of part 3, leaving a shoulder 38 for the mentioned gold cylinder or plastic sheath 6 to bear upon. The original top diameter 54 is about 3.1 mm. In the lower surface 53, a threaded hole allows for the engagement of parts 5 and 3. On the top, a threaded hollow 56 will receive screw 7 that will fix the prosthesis to the assembly. On the outside of this cylinder, four tappered faces 57 are cut at 90 degree angles of each other giving the part a pyramidal shape. The function of these planes is that of securing a perfect interlock with gold cylinder 6, or the material replacing the plastic sheath 6, thus preventing it from rotating. Hole 58 runs through the center of this part for an allen wrench to be used to tighten screw 4 once the final position is achieved. During fabrication the three above mentioned parts 3, 4, and 5, are assembled together: the two large pieces are screwed and cemented to one another having already the titanium screw inside. At the time of its placement on the implanted anchor these parts are treated as a simple and complete assembly. The cavity in which the screw is housed (34, 58) is large enough to allow the easy rotation of the 5 sided end- 10 sided hollow interface while holding the assembly and the implant together.

Figure 1:
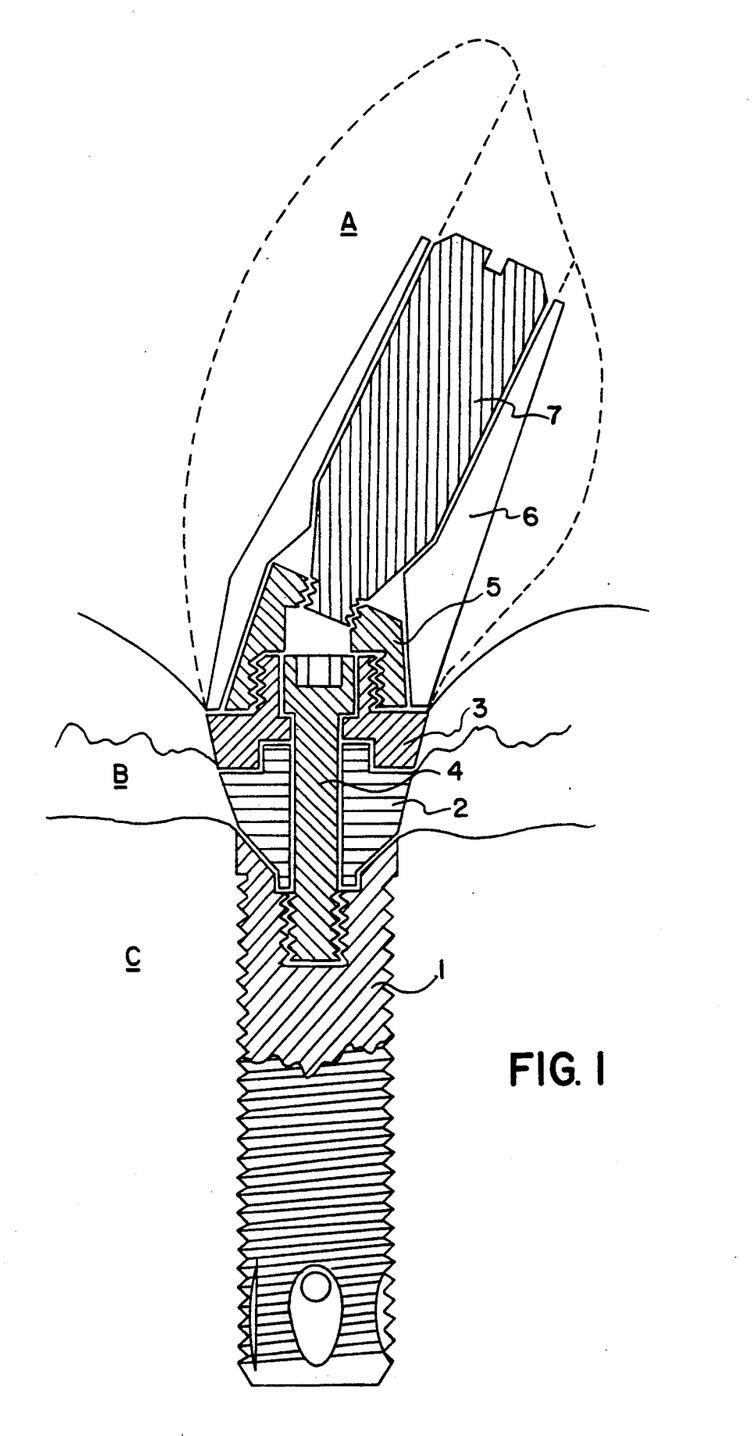
FIG. 1 shows the complete implant 1 and prosthesis A as they appear in relation with the bone C and gum B. In this case a six sided recessed end type implant system is showed with its recessed end implant 1 and its plastic sheath 6.
Figure 2:
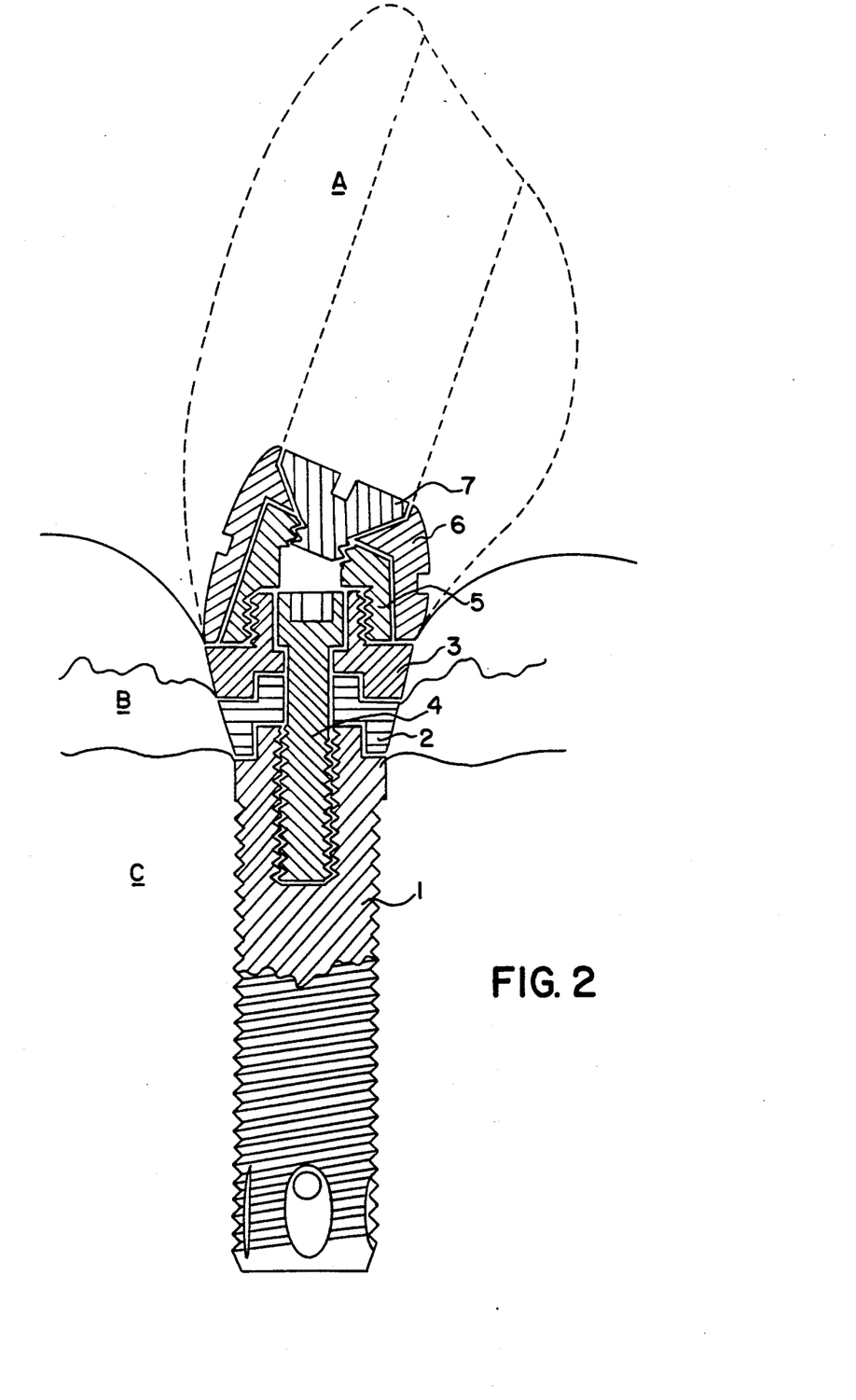
FIG. 2 shows the way the angulated abutment appears when an hexagonal end type implant system is chosen, with its gold cylinder 6 and the six sided implant's outer end 12.
Figure 3A:
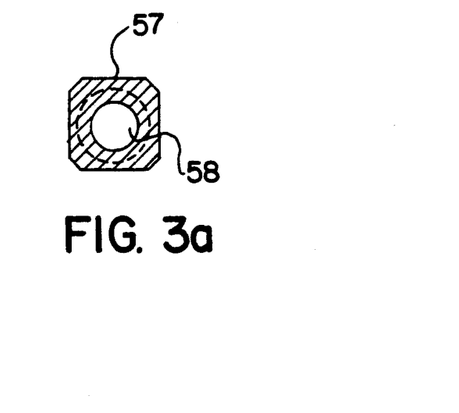
FIGS. 3a-c AND 4a-c show exploded views of the various components, for an hexagonal end type implant, and for a six sided recessed end type implant systems respectively, and are the basis for the following description.
Figure 3B:
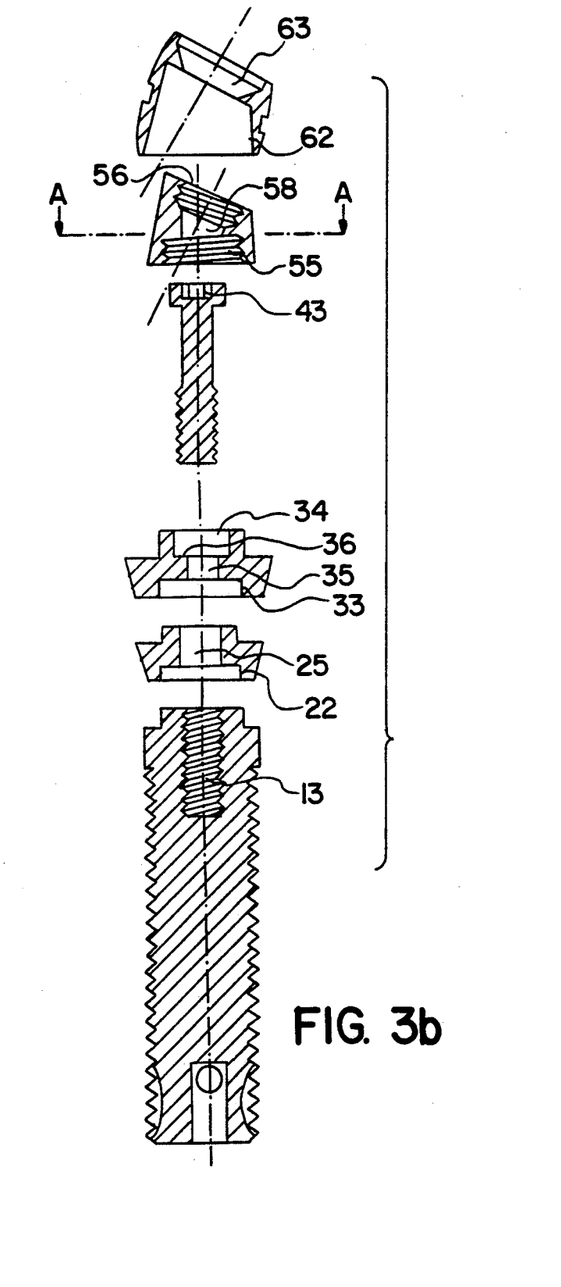
Figure 3C:
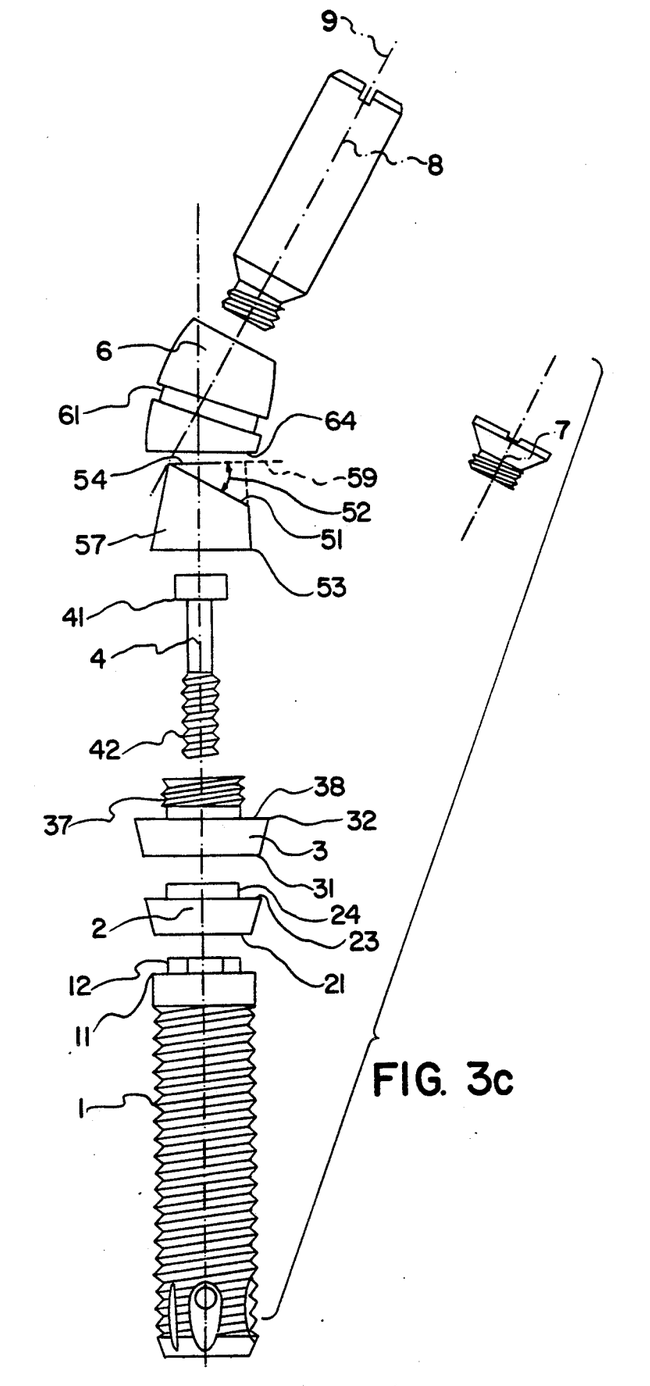

A gold cylinder 6 telescopically covers part 5. It is going to be attached to 5 by means of a fixing gold screw 7 and its function is to serve as the metal base for the final prosthesis to be built upon. It is a slightly tappered cylinder with a groove 61 running around it. Inside this gold cylinder provisions are taken to allow for the following: 1. at the bottom, a cavity 62 is left matching cylinder 5, but with enough clearance as to allow for only the rim of its base 64 to rest on the shoulder 38 left on part 3. This implies that the lower edge of the gold cylinder is cut through a plane that it is not normal to its axis but forms an angle to it as it is the case with part 5 described earlier. A whole set of gold cylinders 6 is required with lower edges cut at different planes to match the proposed series of part 5. 2. at the top, a cavity 63 is left to house gold screw 7 passing through the part and threading into truncated cone 5.

Figure 4A:
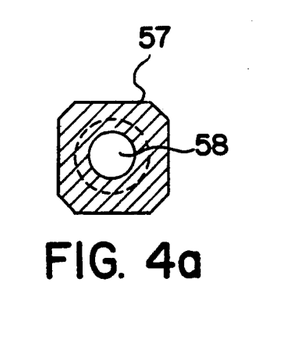
Figure 4B:
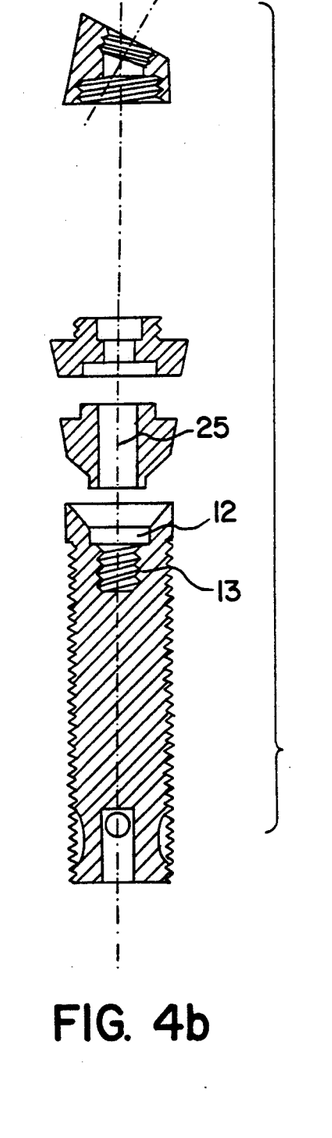
Figure 4C:
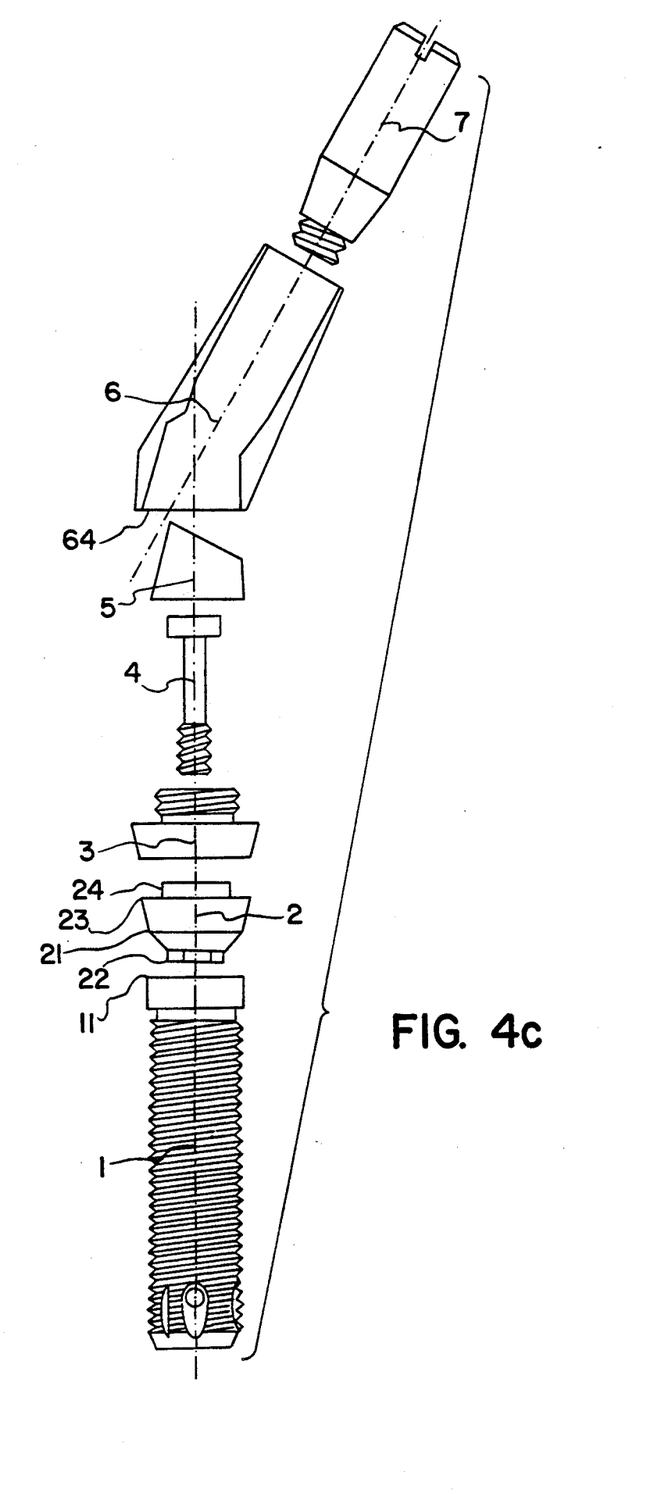

A plastic sheath replaces 6 the gold cylinder if a six sided recessed end type implant system is chosen. It melts away with the waxing material in the moulding process. It also has a cavity for the fixing screw and for the pyramid 5 on which it will be set. Only the rim of its base will rest on the shoulder 38 left on part 3. This implies that the lower edge 64 of the sheath is cut through a plane that forms an angle with its axis as it is the case with the truncated cone 5 described earlier. A whole set of plastic sheaths is required with lower edges cut at different planes to match the mentioned set of cones.

Finally, for an hexagonal end type implant system, a gold flat head, slotted screw 7 is used to hold in place the prosthesis built on the gold cylinder 6. If a six sided recessed end type implant system is used, a commercially available sloted screw 7 with a cylindrical body holds the prosthesis fixed to the rest of the abutment.

When an hexagonal end type implant system is chosen, a slotted guide pin 8 is used to replace the gold screw during the procedure for setting the abutment in the desired direction. Its lower end has a replica of gold screw 7 it replaces.

TABLES 1 AND 2 show the final azimuth angle of part 3, consequently that of the prosthesis, relative to its original position on the implant. It can be seen in both cases, all the different angles that can be obtained.

TABLE 1

Figure 5:
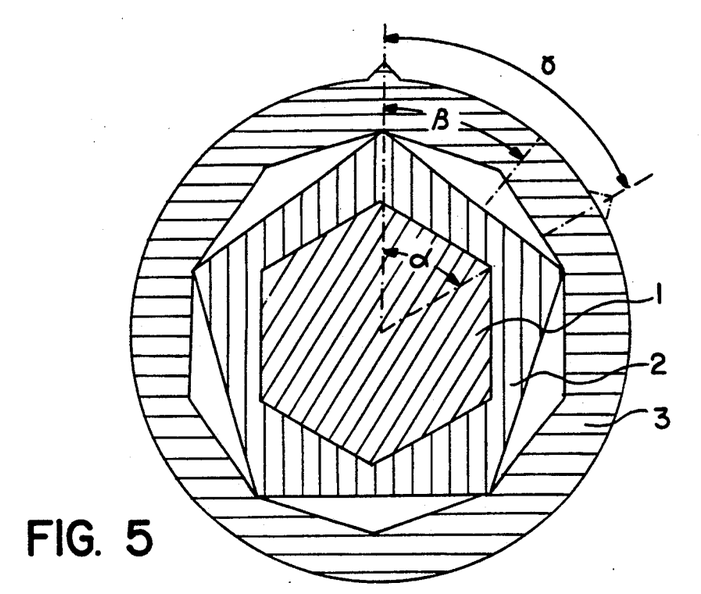
FIGS. 5 AND 6 are representative diagrams showing the angles involved in the combination of parts 1, 2 and 3 for six-sided-recessed and hexagon-protruding end implant type systems respectively. Angle alpha is that obtained rotating part 2 over the implant 1; angle beta is that of the rotation of part 3 over part 2. The combination of these two angles, adding or substracting multiples of one another, give as a result angle gamma which represents the azimuth angle of the final prosthesis' axis from its initial position regarding the implanted anchor.

Azimuth angles (gamma) attainable through the combination of parts 1, 2 and 3.
Thirty different positions, 1 every 12 degrees. See FIG. 5.

| n | n * alpha | (n * alpha) − beta | (n * alpha) + beta | (n * alpha) − (2 * beta) | (n* alpha) + (2 * beta) |
|---|---|---|---|---|---|
| 0 | 0 | 324 | 36 | 288 | 72 |
| 1 | 60 | 24 | 96 | 348 | 132 |
| 2 | 120 | 84 | 156 | 48 | 192 |
| 3 | 180 | 144 | 216 | 108 | 252 |
| 4 | 240 | 204 | 276 | 168 | 312 |
| 5 | 300 | 264 | 336 | 228 | 12 |
| 6 | 360 | 324 | 36 | 288 | 72 |

Angle alpha min. = 60 degrees, from part 2 on an implant with a six sided depressed end
Angle beta min. = 36 degrees, from the interfase of parts 2 and 3

TABLE 2

Figure 6:
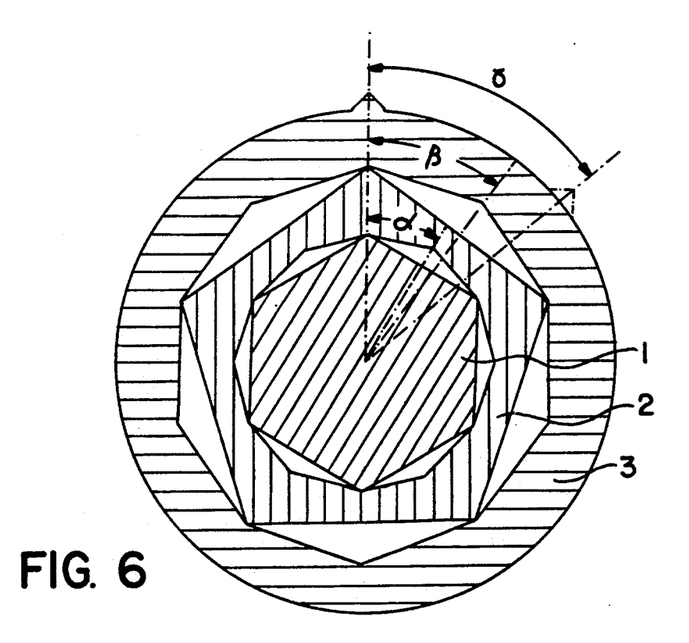

Azimuth angles (gamma) attainable through the combination of parts 1, 2 and 3.
Sixty different positions, 1 every 6 degrees. See FIG. 6.

| n | n * alpha | (n * alpha) − beta | (n * alpha) + beta | (n * alpha) − (2 * beta) | (n * alpha) + (2 * beta) |
|---|---|---|---|---|---|
| 0 | 0 | 324 | 36 | 288 | 72 |
| 1 | 30 | 354 | 66 | 318 | 102 |
| 2 | 60 | 24 | 96 | 348 | 132 |
| 3 | 90 | 54 | 126 | 18 | 162 |
| 4 | 120 | 84 | 156 | 48 | 192 |
| 5 | 150 | 114 | 186 | 78 | 222 |
| 6 | 180 | 144 | 216 | 108 | 252 |
| 7 | 210 | 174 | 246 | 138 | 282 |
| 8 | 240 | 204 | 276 | 168 | 312 |
| 9 | 270 | 234 | 306 | 198 | 342 |
| 10 | 300 | 264 | 336 | 228 | 12 |
| 11 | 330 | 294 | 6 | 258 | 42 |
| 12 | 360 | 324 | 36 | 288 | 72 |

Angle alpha min. = 30 degrees, from part 2 on an implant with a six sided end
Angle beta min. = 36 degrees, from the interfase of parts 2 and 3

I claim:

1. A system for fixing a dental prosthesis to an anchor implanted in the jaw bone of a patient so that a longitudinal axis through said prosthesis is at an angle with respect to a longitudinal axis through said anchor, said system comprising:
   an intermediate abutment member having three component parts being connected to a prosthesis and to said anchor;
   means for rotating two of said component parts with respect to each other whereby said prosthesis can have a plurality of different angular positions with respect to said anchor;
   one of said rotating components having two multi-sided faceted faces adapted to be telescopically inserted into a multi-sided recess at each end to rigidly secure a particular angular position;
   wherein a first of said component parts has a twelve sided first end that is adapted to be received in a hexagonal recess in one end of the anchor; and
   said first of said component parts has a five sided second end that is received in a ten sided recess in a first end of a second of said component parts.

2. A system for fixing a dental prosthesis to an anchor implanted in the jaw bone of a patient so that a longitudinal axis through said prosthesis is at an angle with respect to a longitudinal axis through said anchor, said system comprising:
   an intermediate abutment member having three component parts being connected to a prosthesis and to said anchor;
   means for rotating two of said component parts with respect to each other whereby said prosthesis can have a plurality of different angular positions with respect to said anchor;
   wherein a first of said component parts has a six sided first end that is adapted to be received in a hexagonal recess in one end of the anchor; and
   said first of said component parts has a five sided second end that is received in a ten sided recess in a first end of a second of said component parts.

3. A system for fixing a dental prosthesis to an anchor implanted in the jaw bone of a patient so that a longitudinal axis through said prosthesis is at an angle with respect to a longitudinal axis through said anchor, said system comprising:

an intermediate abutment member having three component parts being connected to a prosthesis and to said anchor;

means for rotating two of said component parts with respect to each other whereby said prosthesis can have a plurality of different angular positions with respect to said anchor;

one of said rotating components having two multi-sided faceted faces adapted to be telescopically inserted into a multi-sided recess at each end to rigidly secure a particular angular position;

wherein the first and second of said component parts are disposed adjacent each other and rotate with respect to each other; said first and second of said component parts each include a cylindrical bore therethrough having a longitudinal axis which is coaxial with the longitudinal axis through said anchor; and screw means extending through the cylindrical bores of the first and second component parts and into said anchor whereby said first and second components are securely attached to said anchor;

said anchor has an outer diameter at the end projecting from said jawbone in which it is implanted, said first of said component parts is constructed of a tapered cylinder with upper and lower surfaces, said lower surface having substantially the same diameter as the outer diameter of the projecting end of the anchor;

said first of said component parts further having a first end projecting from the lower surface of the tapered cylinder for attachment to a recess in the projecting end of the anchor and a second end projecting from the upper surface of the first of said component parts for receipt in a recess in the first end of the second of said component parts; and said second of said component parts is a tapered cylinder having flat upper and lower surfaces and said cylindrical bore extending therethrough, a threaded end is provided on said upper surface of said second of said component parts for attachment to a third of said component parts, and second lower surface of said second of said component parts has a diameter which is substantially equal to the diameter of the upper surface of said first of said component parts.

4. The system as defined in claim 3, wherein said second of said component parts has a recess extending from the upper surface, said recess having a larger diameter than the cylindrical bore whereby a shoulder, formed at the intersection of the recess and the bore, is provided to seat the head of the screw means disposed in the bores of the first and second of said component parts for threaded attachment into the recess in the projecting end of the anchor to attach the intermediate abutment member to the anchor.

5. The system as defined in claim 4, wherein the third of said component parts comprises a truncated, asymmetrical cone having an upper surface disposed at a given angle to a plane normal to a longitudinal axis extending therethrough; said third of said component parts having a bottom surface with a recess extending therein to receive the second end of the second of said component parts; the lower surface of said third of said component parts having a smaller diameter than the upper surface of said second of said component parts whereby when said third of said component parts is engaged against said second of said component parts, a shoulder is formed to support a sheath for connecting said prosthesis to said abutment member.

6. The system as defined in claim 5, wherein the third of said component parts has on its outer cone-shaped surface, four tapered faces cut at 90° angles of each other to form a pyramidal shape, said faces securing the prosthesis connecting the sheath, thus preventing rotation of said prosthesis; and a through hole in the third of said component parts providing access to tighten the screw means.

7. The system as defined in claim 6, wherein said second of said component parts is cemented to said first of said component parts.

8. The system as defined in claim 7, wherein said sheath telescopically covers said third of said component parts and is attached thereto by a fixing screw.

9. The system as defined in claim 8, wherein said sheath includes a cavity extending from a bottom surface thereof enabling the sheath to rest against the upper surface of the third of said component parts, and a cavity extending from the upper surface of said sheath to house a screw which is threadedly received in the recess formed in the upper surface of the third of said component parts.

10. The system as defined in claim 9 wherein said sheath is plastic.

11. The system as defined in claim 9 wherein said sheath is gold.

12. A system for fixing a dental prosthesis to an anchor implanted in the jaw bone of a patient so that a longitudinal axis through said prosthesis is at an angle with respect to a longitudinal axis through said anchor, said system comprising:

an intermediate abutment member having three component parts being connected to said prosthesis and to said anchor;

means for rotating two of said component parts with respect to each other whereby said prosthesis can have a plurality of different angular positions with respect to said anchor;

said first component part has a twelve sided first end that is adapted to be received in a hexagonal recess in one end of the anchor and has a five sided second end that is received in a ten sided recess in a first end of a second of said component parts.

13. A system for fixing a dental prosthesis to an anchor implanted in the jaw bone of a patient so that a longitudinal axis through said prosthesis is at an angle with respect to a longitudinal axis through said anchor, said system comprising:

an intermediate abutment member having three component parts being connected to said prosthesis and to said anchor;

means for rotating two of said component parts with respect to each other whereby said prosthesis can have a plurality of different angular positions with respect to said anchor;

said first component part has a six sided first end that is adapted to be received in a hexagonal recess in one end of the anchor and has a five sided second end that is received in a ten sided recess in a first end of a second of said component parts.

14. A system for fixing a dental prosthesis to an anchor implanted in the jaw bone of a patient so that a longitudinal axis through said prosthesis is at an angle with respect to a longitudinal axis through said anchor, said system comprising:

an intermediate abutment member having three component parts being connected to said prosthesis and to said anchor;

means for rotating two of said component parts with respect to each other whereby said prosthesis can have a plurality of different angular positions with respect to said anchor;

said anchor has an outer diameter at the end projecting from said jawbone in which it is implanted, said first of said component parts is constructed of a tapered cylinder with upper and lower surfaces, said lower surface having substantially the same diameter as the outer diameter of the projecting end of the anchor;

said first of said component parts further having a first end projecting from the lower surface of the tapered cylinder for attachment to a recess in the projecting end of the anchor and a second end projecting from the upper surface of the first of said component parts for receipt in a recess in the first end of the second of said component parts;

said second of said component parts is a tapered cylinder having flat upper and lower surfaces and said cylindrical bore extending therethrough;

a threaded end is provided on said upper surface of said second of said component parts for attachment to a third of said component parts; and second lower surface of said second of said component parts has a diameter which is substantially equal to the diameter of the upper surface of said first of said component parts.

15. The system as defined in claim 14, wherein said second of said component parts has a recess extending from the upper surface, said recess having a larger diameter than the cylindrical bore whereby a shoulder, formed at the intersection of the recess and the bore, is provided to seat the head of the screw means disposed in the bores of the first and second of said component parts for threaded attachment into the recess in the projecting end of the anchor to attach the intermediate abutment member to the anchor.

16. The system as defined in claim 15, wherein the third of said component parts comprise a truncated, asymmetrical cone having an upper surface disposed at a given angle to a plane normal to a longitudinal axis extending therethrough; said third of said component parts having a bottom surface with a recess extending therein to receive the second end of the second of said component parts; the lower surface of said third of said component parts having a smaller diameter than the upper surface of said second of said component parts whereby when said third of said component parts is engaged against said second of said component parts, a shoulder is formed to support a sheath for connecting said prosthesis to said abutment member.

17. The system as defined in claim 16, wherein the third of said component parts has on its outer cone-shaped surface, four tapered faces cut at 90° angles of each other to form a pyramidal shape, said faces securing the prosthesis connecting the sheath, thus preventing rotation of said prosthesis; and a through hole in the third of said component parts providing access to tighten the screw means.

18. The system as defined in claim 17, wherein said second of said component parts is cemented to said first of said component parts.

19. The system as defined in claim 18, wherein said sheath telescopically covers said third of said component parts and is attached thereto by a fixing screw.

20. The system as defined in claim 19, wherein said sheath includes a cavity extending from a bottom surface thereof enabling the sheath to rest against the upper surface of the third of said component parts, and a cavity extending from the upper surface of said sheath to house a screw which is threadedly received in the recess formed in the upper surface of the third of said component parts.

21. The system as defined in claim 20, wherein said sheath is plastic.

22. The system as defined in claim 20, wherein said sheath is gold.

* * * * *